US00PP35214P2

(12) United States Plant Patent
Eggleton et al.

(10) Patent No.: US PP35,214 P2
(45) Date of Patent: Jun. 6, 2023

(54) ***LAVANDULA* PLANT NAMED 'IB61026'**

(50) Latin Name: *Lavandula stoechas pedunculata*
Varietal Denomination: IB61026

(71) Applicant: PLANT GROWERS AUSTRALIA PTY. LTD., Wonga Park (AU)

(72) Inventors: Steven Eggleton, Wonga Park (AU); Howard Bentley, Wonga Park (AU)

(73) Assignee: PLANT GROWERS AUSTRALIA PTY. LTD., Wonga Park (AU)

( * ) Notice: Subject to any disclaimer, the term of this patent is extended or adjusted under 35 U.S.C. 154(b) by 0 days.

(21) Appl. No.: 17/976,781

(22) Filed: Oct. 29, 2022

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 6/502
See application file for complete search history.

*Primary Examiner* — Anne Marie Grunberg
(74) *Attorney, Agent, or Firm* — C. Anne Whealy

(57) ABSTRACT

A new and distinct cultivar of *Lavandula* plant named 'IB61026', characterized by its compact and upright to slightly outwardly slanting plant habit; freely branching growth habit, dense and bushy appearance; freely flowering habit; dark purple-colored flowers with large purplish violet-colored sterile flower bracts arranged on short terminal spikes; and good garden performance.

1 Drawing Sheet

Botanical designation: *Lavandula stoechas pedunculata.* Cultivar denomination: 'IB61026'.

CROSS-REFERENCED TO CLOSELY-RELATED APPLICATIONS

Title: *Lavandula* Plant Named 'IB61016'Inventors: Steven Eggleton & Howard Bentley Filed: Concurrently with this application having applcation Ser. No. 17/976,778

BACKGROUND OF THE INVENTION

The present invention relates to a new and distinct *Lavandula* plant, botanically known as *Lavandula stoechas pedunculata*, commonly referred to as French Lavender and hereinafter referred to by the name 'IB61026'.

The new *Lavandula* plant is a product of a planned breeding program conducted by the Inventors in Wonga Park, Victoria, Australia. The objective of the breeding program was to develop new dense and freely-flowering *Lavandula* plants with attractive plant form and flower coloration and good garden performance.

The new *Lavandula* plant originated from a cross-pollination in October, 2015 of a proprietary selection of *Lavandula stoechas pedunculata* identified as 'Mini Purple', not patented, as the female, or seed, parent with a proprietary selection of *Lavandula stoechas pedunculata* identified as 'Purple Ruffles Selection 2', not patented, as the male, or pollen, patent. The new *Lavandula* plant was discovered and selected by the Inventors as a single flowering plant within the progeny of the stated self-pollination in a controlled greenhouse environment in Wonga Park, Victoria, Australia in October, 2016.

Asexual reproduction of the new *Lavandula* plant by softwood terminal cuttings in a controlled greenhouse environment in Wonga Park, Victoria, Australia since October, 2016 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'IB61026' as a new and distinct *Lavandula* plant:

1. Compact and upright to slightly outwardly slanting plant habit.
2. Freely branching growth habit, dense and bushy appearance.
3. Freely flowering habit.
4. Dark purple-colored flowers with large purplish violet-colored sterile flower bracts arranged on short terminal spikes.
5. Good garden performance.

Plants of the new *Lavandula* differ primarily from plants of the female parent selection in the following characteristics:

1. Plants of the new *Lavandula* have longer and broader sterile flower bracts than plants of the female parent selection.
2. Plants of the new *Lavandula* have darker violet purple sterile flower bracts than plants of the female parent selection.

Plants of the new *Lavandula* differ primarily from plants of the male parent selection in the following characteristics:

1. Plants of the new *Lavandula* have shorter inflorescences than plants of the male parent selection.
2. Plants of the new *Lavandula* have broader sterile flower bracts than plants of the male parent selection.
3. Plants of the new *Lavandula* have shorter peduncles than plants of the male parent selection.

Plants of the new *Lavandula* differ primarily from plants of *Lavandula stoechas pedunculata*, 'IB61016', disclosed in a U.S. Plant Patent application filed concurrently having application Ser. No. 17/976,778, in the following characteristics:

1. Plants of the new *Lavandula* are slightly larger than plants of 'IB61016'.
2. Plants of the new *Lavandula* have more flowers per inflorescence than plants of 'IB61016'.
3. Plants of the new *Lavandula* have longer and broader sterile flower bracts than plants of 'IB61016'.

Plants of the new *Lavandula* can also be compared to plants of the *Lavandula stoechas* 'Blueberry Ruffles', disclosed in U.S. Plant Pat. No. 18,305. In side-by-side comparisons, plants of the new *Lavandula* differ primarily from plants of 'Blueberry Ruffles' in the following characteristics:

1. Plants of the new *Lavandula* are upright to slightly outwardly slanting whereas plants of 'Blueberry Ruffles' are upright.
2. Plants of the new *Lavandula* and 'Blueberry Ruffles' differ in sterile flower bract color as sterile flower bracts of plants of the new *Lavandula* are darker purplish violet in color than sterile flower bracts of plants of 'Blueberry Ruffles'.
3. Plants of the new *Lavandula* have shorter peduncles than plants of 'Blueberry Ruffles'.

Plants of the new *Lavandula* can also be compared to plants of *Lavandula stoechas* 'Purpleberry Ruffles', not patented. In side by side comparisons, plants of the new *Lavandula* and 'Purpleberry Ruffles' differ primarily in sterile flower bract size as plants of the new *Lavandula* have longer and broader inflorescences than plants of 'Purpleberry Ruffles'.

BRIEF DESCRIPTION OF THE PHOTOGRAPH

The accompanying photograph illustrates the overall appearance of the new *Lavandula* plant showing the colors as true as it is reasonably possible to obtain in colored reproductions of this type.

Colors in the photograph may differ slightly from the color values cited in the detailed botanical description which accurately describe the colors of the new *Lavandula* plant.

The photograph is a side perspective view of a typical flowering plant of 'IB61026' grown in a container.

DETAILED BOTANICAL DESCRIPTION

The aforementioned photograph and following observations, measurements and values describe plants grown during the summer in an outdoor nursery in Fort Worth, Tex. and under cultural practices typical of commercial *Lavandula* production. During the production of the plants, day temperatures ranged from 35° C. to 40° C. and night temperatures ranged from 24° C. to 35° C. Plants were six months old when the photograph and the description were taken. In the description, color references are made to The Royal Horticultural Society Colour Chart, 2015 Edition, except where general terms of ordinary dictionary significance are used.

Botanical classification: *Lavandula stoechas pedunculata* 'IB61026'.

Parentage:

*Female, or seed, parent.*—Proprietary selection of *Lavandula stoechas pedunculata* identified as 'Mini Purple', not patented.

*Male, or pollen, parent.*—Proprietary selection of *Lavandula stoechas pedunculata* identified as 'Purple Ruffles Selection 2', not patented.

Propagation:

*Type.*—Terminal softwood vegetative cuttings.

*Time to initiate roots, summer.*—About ten days at temperatures about 24° C.

*Time to initiate roots, winter.*—About twelve days at temperatures about 21° C.

*Time to produce a rooted young plant, summer.*—About 24 to 28 days at temperatures ranging from 23° C. to 26° C.

*Time to produce a rooted young plant, winter.*—About 35 to 40 days at temperatures ranging from 15° C. to 18° C.

*Root description.*—Fine, fibrous; typically white to light brown in color, actual color of the roots is dependent on substrate composition, water quality, fertilizer type and formulation.

*Rooting habit.*—Freely branching; medium density.

Plant description:

*Plant and growth habit.*—Herbaceous perennial; compact and upright to slightly outwardly slanting plant habit; roughly globular to broadly ovate in overall shape; moderately vigorous growth habit; relatively rapid growth rate; flowers arranged in verticillasters on terminal spikes; freely branching habit, dense and bushy appearance.

*Plant height, soil level to top of foliar plane.*—About 15.5 cm.

*Plant height, soil level to top of floral plane.*—About 18 cm.

*Plant width.*—About 21.5 cm.

*Lateral branch description.*—Quantity per plant: About eight to ten primary lateral branches each with potentially two secondary branches developing at every node during the flowering season. Length: About 9.5 cm. Diameter: About 2 mm. Internode length: About 1.4 cm. Strength: Moderately strong; flexible. Aspect: Upright to slightly outwardly. Texture and luster: Densely tomentose; slightly glossy. Color, developing: Close to 144A to 144C. Color, developed: Close to 144B to 144C.

*Leaf description.*—Arrangement: Opposite, simple; sessile. Length, largest leaves: About 3.5 cm. Width, largest leaves: About 6.5 mm. Shape: Linear. Apex: Sharply acute. Base: Cuneate. Margin: Entire; slightly to moderately revolute. Texture and luster, upper surface: Densely pubescent; matte. Texture and luster, lower surface: Moderately to densely pubescent; matte. Fragrance: Strongly aromatic, pungent. Venation pattern: Pinnate. Color: Developing leaves, upper surface: Close to 137B. Developing leaves, lower surface: Close to 138B. Fully expanded leaves, upper surface: Close to NN137B; venation, close to 144A. Fully expanded leaves, lower surface: Close to 137B; venation, close to 138A.

Flower description:

*Flower type, arrangement and habit.*—Small single salverform flowers arranged in verticillasters on terminal cylindrical spikes; freely flowering habit with about 70 to 90 flowers developing in seven to eight whorls per inflorescence and numerous inflorescences developing per plant during the flowering season; flowers with two-lobed upper lip and three-lobed lower lip; flowers face mostly outwardly on the spike.

*Natural flowering season.*—Relatively long flowering period; continuous from late winter to late spring/early summer in Australia.

*Flower longevity on the plant.*—Inflorescences last about one month on the plant; flowers not persistent.

*Fragrance.*—Resinous, aromatic and pungent.

*Flower buds.*—Length: About 7.5 mm. Diameter: About 4 mm. Shape: Ovoid. Color: Close to 143A.

*Inflorescence height.*—About 2.2 cm, excluding terminal bracts.

*Inflorescence diameter.*—About 1.4 cm, excluding terminal bracts.

*Flower diameter.*—About 2 mm.

*Flower depth (height).*—About 4.5 mm, including tube.

*Flower tube length.*—About 3 mm.

*Flower tube diameter.*—Less than 1 mm.

*Petals.*—Quantity and arrangement: Upper lip, two-lobed and lower lip, three-lobed. Length, upper and lower lips: About 0.9 mm. Width, upper and lower lips: About 1.1 mm. Shape, upper lip: Obovate. Shape, lower lip: Ovate. Apex, upper and lower lips: Obtuse, rounded. Margin, upper and lower lips: Entire; slightly undulate. Texture and luster, upper (inner) surface, upper and lower lips: Smooth, glabrous; slightly velvety; matte. Texture and luster, lower (outer) surface, upper and lower lips: Smooth, glabrous; slightly velvety; slightly glossy. Color, upper and lower lips: When opening, upper (inner) and lower (outer) surfaces: Close to NN155D variably overlain with close to N186B. Fully opened, upper (inner) and lower (outer) surfaces: Close to N186B to N186C; color does not change with subsequent development.

*Basal flower bracts.*—Quantity and arrangement: Each group of flowers is subtended by a single basal flower bract. Length: About 1.1 cm. Width: About 8 mm. Shape: Cordate. Apex: Cuspidate. Base: Cordate. Margin: Entire. Texture, upper and lower surfaces: Smooth, glabrous. Color, upper and lower surfaces: Translucent, close to 157D with venation, close to 143A.

*Sterile flower bracts.*—Quantity and arrangement: About four to six sterile flower bracts at apex of spike. Length: About 3.6 cm. Width: About 2.2 cm. Shape: Broadly obovate; ruffled appearance. Apex: Broadly acute. Base: Cuneate. Margin: Entire; undulate. Texture and luster, upper and lower surfaces: Smooth, glabrous; matte. Color, upper and lower surfaces: Close to between 77A and 86B; main vein, close to 144A; color becoming closer to N75A and 76A with subsequent development.

*Sepals.*—Quantity and arrangement: Five, fused into a campanulate tube. Calyx length: About 7 mm. Calyx diameter: About 3.5 mm. Shape: Lanceolate. Apex: Acute. Margin: Entire. Texture and luster, upper (inner) and lower (outer) surfaces: Densely pubescent; matte. Color, upper (inner) and lower (outer) surfaces: Close to 143A.

*Peduncles.*—Length: About 5.2 cm. Diameter: About 2 mm. Aspect: Mostly upright to slightly outwardly slanting. Strength: Moderately strong to strong; flexible. Texture and luster: Pubescent; matte. Color: Close to 144A to 144B.

*Reproductive organs.*—Stamens: Quantity per flower: Four. Anther shape: Reniform. Anther color: Close to 157D. Pollen amount: None observed. Pistils: Quantity per flower: One. Stigma shape: Club-shaped. Stigma color: Close to N79A. Ovary color: Close to 143A to 143B.

*Seeds and fruits.*—To date, seed and fruit production has not been observed on plants of the new *Lavandula*.

Pathogen & pest resistance: To date, plants of the new *Lavandula* have not been observed to be resistant to pathogens and pests common to *Lavandula* plants.

Garden performance: Plants of the new *Lavandula* have exhibited good garden performance and to tolerate rain and wind and temperatures ranging from 0° C. to 42° C.

It is claimed:

1. A new and distinct *Lavandula* plant named 'IB61026' as illustrated and described.

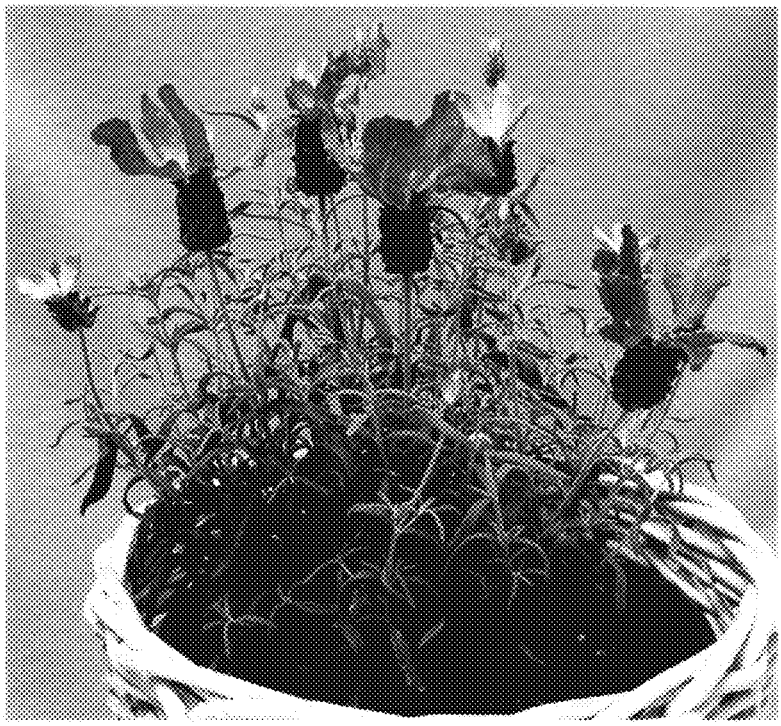

* * * * *